(12) United States Patent
Homola et al.

(10) Patent No.: US 7,973,933 B2
(45) Date of Patent: Jul. 5, 2011

(54) METHOD FOR SPECTROSCOPY OF SURFACE PLASMONS IN SURFACE PLASMON RESONANCE SENSORS AND AN ELEMENT FOR THE USE OF THEREOF

(76) Inventors: Jiri Homola, Prague (CZ); Olga Telezhnikova, Prague (CZ); Jakub Dostalek, Prague (CZ)

(*) Notice: Subject to any disclaimer, the term of this patent is extended or adjusted under 35 U.S.C. 154(b) by 250 days.

(21) Appl. No.: 11/795,184

(22) PCT Filed: Jan. 12, 2006

(86) PCT No.: PCT/IB2006/050118
§ 371 (c)(1),
(2), (4) Date: Jul. 11, 2007

(87) PCT Pub. No.: WO2007/085913
PCT Pub. Date: Aug. 2, 2007

(65) Prior Publication Data
US 2008/0144027 A1    Jun. 19, 2008

(30) Foreign Application Priority Data

Jan. 12, 2005  (CZ) .................................... 2005-19

(51) Int. Cl.
*G01N 21/55* (2006.01)
(52) U.S. Cl. ...................................... 356/445
(58) Field of Classification Search ............... 356/445, 356/448, 326, 328, 369
See application file for complete search history.

(56) References Cited

U.S. PATENT DOCUMENTS

| 4,915,482 A * | 4/1990 | Collins et al. .................. 359/276 |
| 5,455,178 A * | 10/1995 | Fattinger ....................... 436/164 |
| 5,598,267 A | 1/1997 | Sambles et al. |
| 2004/0218184 A1* | 11/2004 | Jorgenson et al. ............. 356/419 |
| 2005/0079635 A1* | 4/2005 | Norman ......................... 436/514 |

FOREIGN PATENT DOCUMENTS

| EP | 1 424 549 | 6/2004 |
| JP | 2002-357542 | 12/2002 |
| WO | WO03014711 | * 2/2003 |

OTHER PUBLICATIONS

Jory et al., "Development Of a Prototype Gas Sensor Using Surface Plasmon Resonance on Gratings," Sensors and Actuators B. vol. 17, pp. 203-209 (1994).
Dostalek et al., "Rich Information Format Surface Plasmon Resonance Biosensor Based On Array Of Diffraction Gratings.," Sensors and Actuators B, vol. 107, pp. 154-161 (Nov. 2004).

* cited by examiner

*Primary Examiner* — Tarifur Chowdhury
*Assistant Examiner* — Michael LaPage
(74) *Attorney, Agent, or Firm* — Patrick J.S. Inouye; Krista A. Wittman

(57) ABSTRACT

A method and system for spectroscopy of surface plasmons is presented. An electromagnetic wave is made incident on a diffraction grating. Surface plasmons are excited on a medium coincident to the diffraction grating and dispersion of a wavelength spectrum of the electromagnetic wave are simultaneously performed through diffraction. Changes in spatial distribution of intensity in the wavelength spectrum of the diffracted electromagnetic wave due to the excitation of the surface plasmons are measured.

28 Claims, 3 Drawing Sheets

METHOD FOR SPECTROSCOPY OF SURFACE PLASMONS IN SURFACE PLASMON RESONANCE SENSORS AND AN ELEMENT FOR THE USE OF THEREOF

TECHNICAL FIELD

The present invention relates in general to a method for spectroscopy and, in particular to a method for spectroscopy of surface plasmons in surface plasmon resonance sensors and an element for the use of thereof.

BACKGROUND ART

Sensors belong to modern devices for measuring physical, chemical and biological quantities.

Modern sensors such as electrical, optical and mechanical sensors rely on various methods. One of the approaches used in optical sensors is the spectroscopy of surface plasmons. Surface plasmons are electromagnetic waves, which can be excited at an interface between a metal and a dielectric medium (Raethec Surface plasmons on smooth and rough surfaces and on gratings, Springer-Verlag, Berlin, 1988). As the electromagnetic field of surface plasmons is highly localized at the surface of the metal, surface plasmons are extremely sensitive to changes in optical parameters occurring in the vicinity of the surface of the metal. In optical sensors, surface plasmons are usually optically excited with an electromagnetic wave in the visible or near infrared spectrum. The resonant condition for excitation of the surface plasmons with an electromagnetic wave depends on a refractive index of the dielectric medium in the proximity of the metal surface. Therefore, variations in the refractive index can be monitored from the changes in the interaction between an electromagnetic wave and a surface plasmon. Surface plasmon resonance (SPR) sensors can be used as highly sensitive refractometers and can also be applied to the study of biomolecules and their interactions and for detection of chemical and biological compounds. In these applications, SPR sensors are combined with biorecognition elements, which specifically interact with an analyte (e.g., antibody, enzymes, and DNA). The interaction between the immobilized biorecognition element on the sensor surface and the analyte in a liquid sample increases a refractive index in the proximity of the surface of the sensor. This refractive index change can be detected by means of optically excited surface plasmons.

There are numerous configurations of surface plasmon resonance (SPR) sensors. These include configurations employing prism couplers (Sensors and Actuators, 4 (1983) 299-304; Electronics Letters, 23 (1988) 1469-1470), grating couplers (Sensors and Actuators B, 8 (1992) 155-160), optical fibers (Sensors and Actuators B, 12 (1993) 213-220; Analytical Chemistry, 66 (1994) 963-970) and integrated optical waveguides (Sensors and Actuators B, 12 (1993) 213-220; Analytical Chemistry, 66 (1994) 963-970). In grating-based SPR sensors, an interaction between an electromagnetic wave and a surface plasmon is detected by measuring changes in intensity (Biosensors, 3 (1987/88) 211-225), angular spectrum (American Laboratory, 33 (2001) 37-40) or wavelength spectrum (Measurements and Science Technology, 6 (1995) 1193-1200) of an electromagnetic wave reflected from a grating coupler. For parallel detection of multiple chemical or biological compounds, or for parallel monitoring of their interactions, multichannel SPR sensors are used. In multichannel SPR sensors, using grating couplers, the resonant interaction between an electromagnetic wave and surfaces surface plasmons can be detected in a spatial distribution of an angular reflected spectrum (American Laboratory, 33 (2001) 37-40). Recently, a method for multichannel SPR sensor based on a prism coupler and sequential excitation of surface plasmons was described in Czech patent No. 291 728 (J. Čtyroký, J. Dostálek, J. Homola).

SUMMARY OF THE INVENTION

This invention concerns surface plasmon resonance sensors with a wavelength interrogation and grating coupler. The invention consists of an SPR sensor method for simultaneous excitation of surface plasmons with an electromagnetic wave and dispersion of a spectrum of the electromagnetic wave. In this method, the electromagnetic wave is made incident on a diffraction grating where it is diffraction coupled to surface plasmons. Simultaneously, the wavelength spectrum of the electromagnetic wave is spatially dispersed through diffraction on the grating. Changes in the spectrum of the electromagnetic wave induced by the excitation of the surface plasmons are detected with the method measuring spectral distribution of the intensity of the dispersed electromagnetic wave.

For this method, an electromagnetic wave is emitted from two or more monochromatic light-sources or from a source of polychromatic light. The electromagnetic wave is made incident on a surface of a sensor element with a diffraction grating, where it excites surface plasmons within a narrow band of wavelengths. The excitation of the surface plasmons is accompanied with a change in intensity of a diffracted electromagnetic wave within this wavelength band. Radiation of different wavelengths is diffracted away from the grating under different angles. Therefore, changes in the wavelength spectrum of the electromagnetic wave are converted to variations in the spatial distribution of intensity of the diffracted electromagnetic wave. These changes are detected with a system allowing the measurement of the spatial distribution of the electromagnetic radiation (such detection system is further referred to as a position-sensitive detector). The measurement of the intensity distribution of the diffracted electromagnetic radiation enables monitoring of evolution of the resonant interaction between the electromagnetic wave and the surface plasmons, and thus allows determining the sensor response.

The method is based on a sensor element, which works both as a coupling and dispersing element. This sensor element encompasses a diffraction grating on which surface plasmons are excited with an electromagnetic wave incident on its surface, and a wavelength spectrum of the electromagnetic wave is dispersed into different angles. This method is principally different from existing SPR sensors with wavelength interrogation in which the sensor element serves only for excitation of surface plasmons, and the spectral analysis of the electromagnetic wave is performed separately using a spectrograph with an independent dispersive element. The herein described method significantly simplifies the construction of SPR sensors.

The method for SPR sensor detection relies on a sensor element. This sensor element enables excitation of surface plasmons and angular dispersion of a wavelength spectrum, and can be realized as follows. An electromagnetic wave in visible or near infrared spectrum propagates in a medium and under an angle of incidence. It is incident at the sensor element with a diffraction grating and a metal layer. On the metal surface, there is a dielectric medium. On the relief diffraction grating, a narrow wavelength band of the electromagnetic wave is diffraction-coupled to the surface plasmon at an interface between the metal and the dielectric medium. Simultaneously, the electromagnetic wave is diffracted into a divergent beam. In the divergent beam, an electromagnetic radiation of different wavelengths propagates away from the grating under different angles. Within the diffracted beam, the intensity of the electromagnetic radiation is changed within the narrow wavelength band due to the excitation of the surface plasmons. The divergent beam is made incident on a position-sensitive detector, which measures a spatial distribution of electromagnetic intensity. The excitation of the surface plasmons on the diffraction grating is manifested as a change in the intensity distribution of the diffracted electromagnetic beam, which is detected with the position-sensitive detector.

The method for an SPR sensor using the above described sensor element can be extended for a multichannel sensor configuration by the following embodiments:

In a first embodiment, an electromagnetic wave is made simultaneously incident on multiple sensing areas with a diffraction grating. These sensor areas are arranged parallel to the direction of propagation of surface plasmons. At different sensing areas, the electromagnetic wave is diffracted to a series of spatially separated diverging electromagnetic beams propagating away from the surface of the sensor element. These electromagnetic beams are incident on different areas of a position-sensitive detector.

In a second embodiment, the electromagnetic wave is made incident on the multiple sensing areas with the diffraction grating. These sensor areas are arranged perpendicular to the direction of propagation of the surface plasmons. At different sensing areas, the electromagnetic wave is diffracted to a series of spatially separated diverging light beams propagating away from the surface of the sensor element. These light beams are incident at different areas of the position-sensitive detector.

In a third embodiment, the electromagnetic wave is normally incident on multiple sensing areas with diffraction gratings. In different sensing areas, different diffraction gratings are oriented differently with respect to the center of the position-sensitive detector. At the different sensing areas, the electromagnetic wave is diffracted to a series of spatially separated diverging electromagnetic beams propagating away from the surface of the sensor element. Owing to the different orientation of the diffraction gratings in the different sensing areas, the diffracted diverging electromagnetic beams are projected on different areas of the position-sensitive detector.

The sensor element can be coated in at least one area by a layer with molecules for the detection or study of an interaction of chemical or biological substances present in a sample, which is in contact with the surface of the sensor element.

The sensor element for the method presented herein can be fabricated from glass by means of methods such as cutting, lapping, polishing, and etching. Additionally, it can be fabricated from polymers by methods such as injection molding or hot embossing. Thin metal layers supporting the surface plasmons (e.g., gold, silver) and other optical layers can be prepared by methods such as vacuum evaporation or sputtering. As the position-sensitive detector, linear or two-dimensional detectors, such as a CCD, PDA or CMOS detector can be used. As a source of electromagnetic radiation light emitting diodes (LED), filament lamps or discharge lamps can be employed.

DESCRIPTION OF DRAWINGS

The invention is explained in the following drawings.

EXAMPLES

Example 1

Figure 1:
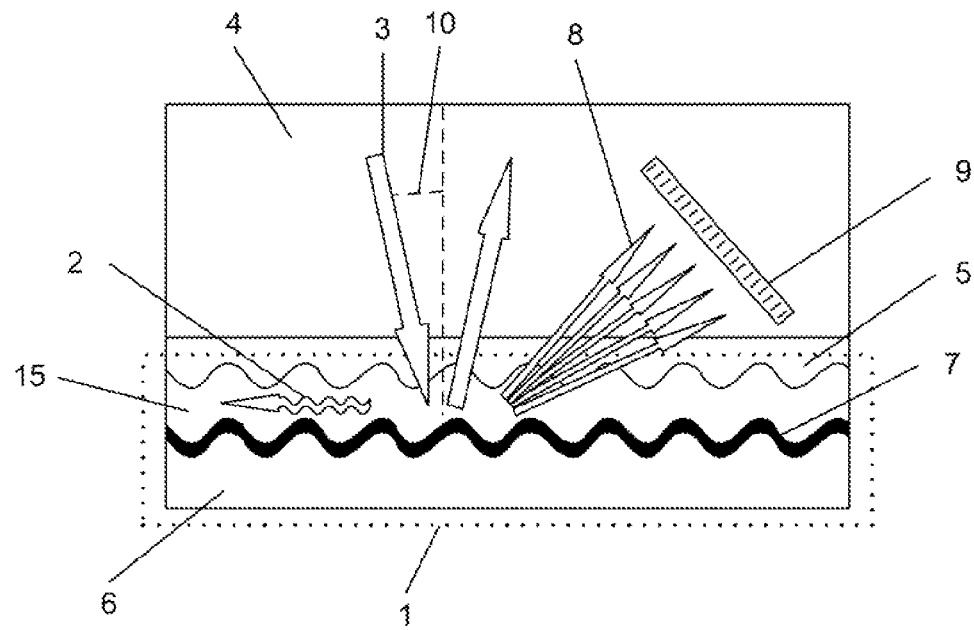
FIG. 1 depicts a method for SPR sensor detection using a sensor element 1 on which a relief diffraction grating 6 is prepared. On the diffraction grating 6, an incident electromagnetic wave 3 is coupled to surface plasmons 2 and is diffracted into a diverging beam 8. In the diffracted beam 8, electromagnetic radiation at different wavelengths is propagated from a surface of the sensor element 1 at different directions. Excitation of the surface plasmons and dispersion of the electromagnetic wave 3 into the diverging beam 8 is realized through different diffraction orders of the grating 6.

FIG. 1 shows an embodiment of a method for SPR sensor detection using a sensor element 1 with a diffraction grating 6 which enables diffraction-coupling of an electromagnetic wave 3 to surface plasmons 2 and angular dispersion of a wavelength spectrum of the electromagnetic wave 3. The collimated electromagnetic wave 3 is made incident in an optical medium 4 at the sensor element 1 under an angle 10. On the top of the sensor element 1, there is a periodic relief diffraction grating 6 coated with a metal layer 7. The grating 6 with the metal layer 7 is in contact with a dielectric medium 5. At an interface between the metal 7 and the dielectric medium 5, the electromagnetic wave 3 excites the surfaces plasmons 2 within a narrow band of wavelengths through the second diffraction order. The excitation of the surface plasmons 2 is accompanied with absorption of energy of the electromagnetic wave 3 at these wavelengths. Simultaneously, upon the incidence on the relief diffraction grating 6, the electromagnetic wave 3 is diffracted into the first diffraction order, which forms a diverging electromagnetic beam 8. In this electromagnetic beam 8, radiation of different wavelengths propagates away from the surface of the sensor element 1 at different angles. In the dispersed wavelength spectrum, an intensity change occurs at wavelengths at which the electromagnetic wave 3 is coupled to the surface plasmons 2. The angular dispersed wavelength spectrum can be measured using a position-sensitive detector 9.

Example 2

Figure 2:
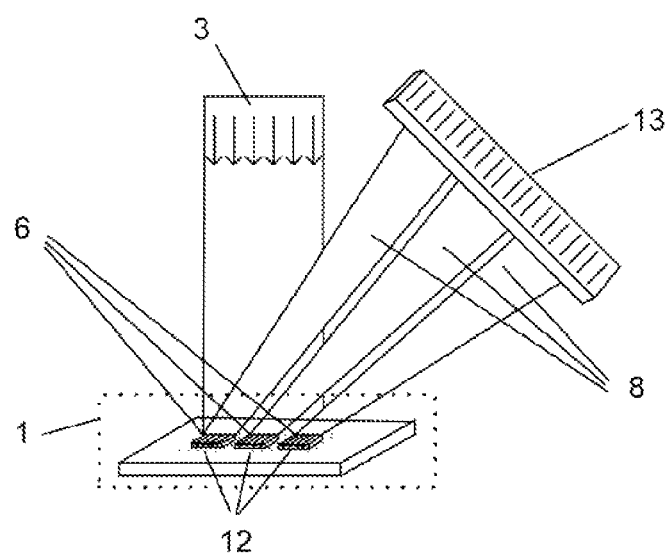
FIG. 2 shows a method for multichannel SPR sensor detection using a sensor element 1 with multiple sensing areas 12 with a relief diffraction grating 6. At the different sensing areas 12, an electromagnetic wave 3 is diffracted to a series of spatially separated diverging electromagnetic beams 8 propagating away from a surface of the sensor element 1. These electromagnetic beams 8 are incident on different areas of a linear position-sensitive detector 13.

FIG. 2 shows an embodiment of a method for multichannel SPR sensor detection using a sensor element 1 with multiple sensing areas 12 with a diffraction grating 6, which enables the coupling of an electromagnetic wave 3 to surface plasmons 2 and angular dispersion of a wavelength spectrum of the electromagnetic wave 3. The collimated electromagnetic wave 3 is made simultaneously incident on multiple sensing areas 12, which are arranged parallel to the direction of propagation of the surface plasmons. Through diffraction on the gratings 6, in different sensing areas 12, the electromagnetic wave 3 is coupled to spatially separated divergent electromagnetic beams 8. The diffracted beams 8 propagate away from a surface of the sensor element 1 and are incident on different areas of a linear position-sensitive detector 13. In each diffracted beam 8, electromagnetic radiation of different wavelengths propagates away from the surface of the sensor element 1 under different angles. Spatial separation of the diffracted beams 8 can be achieved by changing a period of the diffraction grating 6 in each of the sensor areas 12.

Example 3

Figure 3:
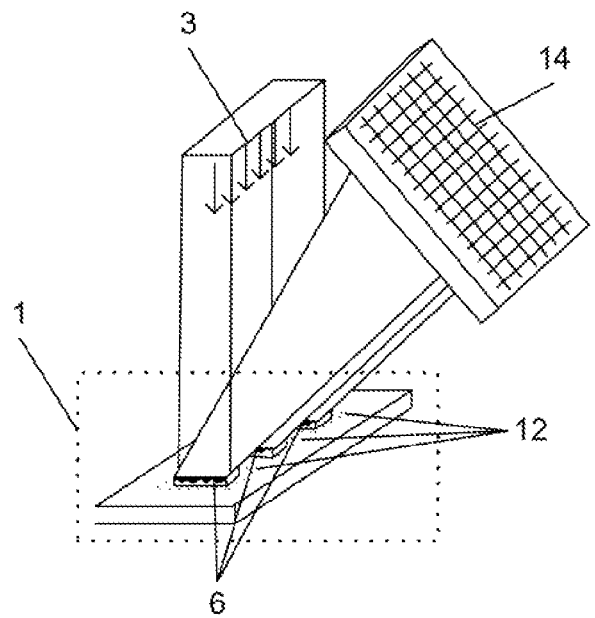
FIG. 3 shows a method for multichannel SPR sensor detection using a sensor element 1 with multiple sensing areas 12 with a diffraction grating 6. At the different sensing areas 12, an electromagnetic wave 3 is diffracted to a series of spatially separated diverging electromagnetic beams 8 propagating away from a surface of the sensor element 1. These electromagnetic beams 8 are incident on different areas of a two-dimensional position-sensitive detector 14.

FIG. 3 shows an embodiment of a method for multichannel SPR sensor detection using a sensor element 1 with multiple sensing areas 12 with a diffraction grating 6 which enables the coupling of an electromagnetic wave 3 to surface plasmons 2 and angular dispersion of a wavelength spectrum of the electromagnetic wave 3. The collimated electromagnetic wave 3 is made simultaneously incident on the multiple sensing areas 12, which are arranged perpendicularly to the direction of propagation of the surface plasmons. Through diffraction on the gratings 6, at different sensing areas 12, the electromagnetic wave 3 is coupled to spatially separated divergent electromagnetic beams 8. The diffracted beams 8 propagate away from a surface of the sensor element 1 and are incident on different areas of a two-dimensional position-sensitive detector 14. In each diffracted beam 8, electromagnetic radiation of different wavelengths propagates away from the surface of the sensor element 1 at a different angle.

Example 4

Figure 4:
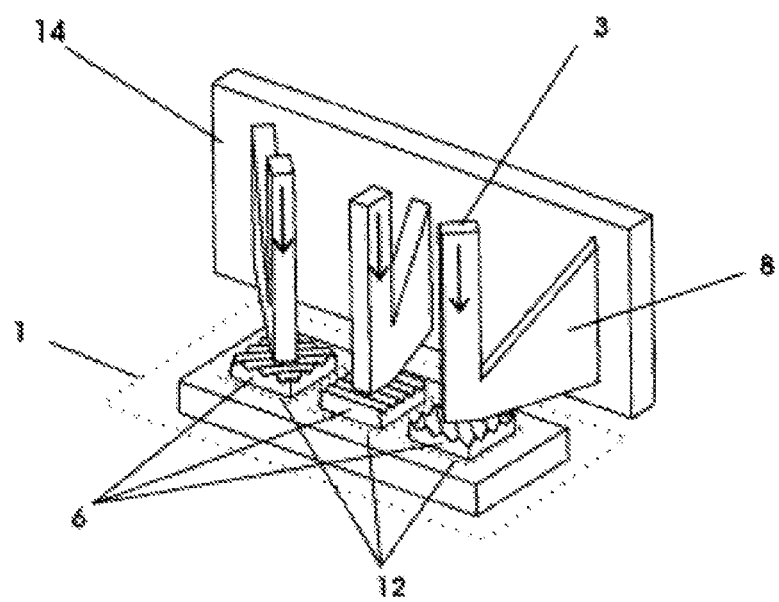
FIG. 4 shows a method for multichannel SPR sensor detection using a sensor element 1 with multiple sensing areas 12 with a diffraction grating 6. In the different sensing areas 12, the diffraction gratings 6 are oriented differently. At the different sensing areas 12, an electromagnetic wave 3 is diffracted to a series of spatially separated diverging electromagnetic beams 8 propagating away from a surface of the sensor element 1. Owing to the different orientation of the diffraction gratings 6 located in the different sensing areas 12, the diffracted diverging electromagnetic beams 8 are projected on different areas of a two-dimensional position-sensitive detector 14.

FIG. 4 shows an embodiment of a method for multichannel SPR sensor detection using a sensor element 1 with multiple sensing areas 12, each with a diffraction grating 6 which enable coupling of an electromagnetic wave 3 to surface plasmons 2 and angular dispersion of a wavelength spectrum of the electromagnetic wave 3. The collimated electromagnetic wave 3 is made simultaneously incident on the multiple sensing areas 12. In different sensing areas 12, the diffraction gratings are oriented different with respect to a center of a two-dimensional position-sensitive detector 14. Through diffraction on the diffraction gratings 6, at different sensing areas 12, the electromagnetic wave 3 is coupled to spatially separated divergent electromagnetic beams 8. The diffracted beams 8 propagate away from a surface of the sensor element 1 and are incident on different areas of the two-dimensional position-sensitive detector 14. In each diffracted beam 8, electromagnetic radiation of different wavelengths propagates away from the surface of the sensor element 1 at a different angle.

Example 5

Figure 5:
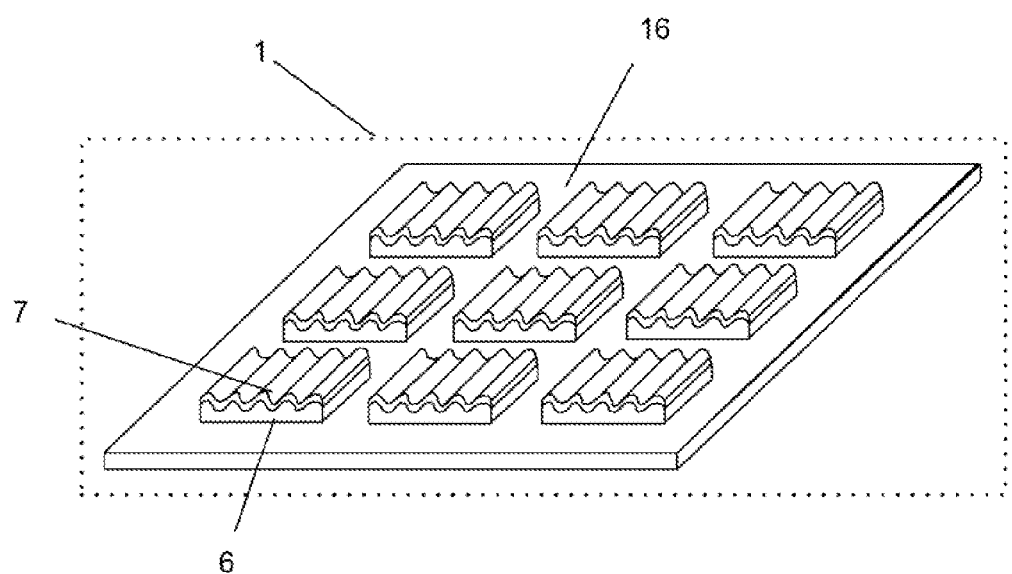
FIG. 5 shows a sensor element 1 as a planar slide 16 with an array of diffraction gratings 6.

FIG. 5 depicts an embodiment of a sensor element 1 for an SPR sensor method described herein in a form of a planar slide 16 with an array of sensing areas 12. In each sensing area 12, there is a diffraction grating 6 for coupling of an electromagnetic wave 3 to surface plasmons 2 and for an angular dispersion of a wavelength spectrum of the electromagnetic wave 3.

INDUSTRIAL APPLICABILITY

The method according to the invention can be used in numerous areas, such as medical diagnostics (detection of biomedical markers), the pharmaceutical industry (drug development), the food industry (quality control, detection of harmful contaminants, foodborne pathogens and toxins), environmental protection (monitoring of pollution of water and atmosphere), and warfare and security (detection of harmful compounds).

The invention claimed is:

1. A method for spectroscopy of surface plasmons, comprising:
    making a collimated electromagnetic wave incident on a diffraction grating;
    simultaneously exciting surface plasmons and causing dispersion of a wavelength spectrum of the electromagnetic wave through diffraction on the diffraction grating, wherein the surface plasmons are excited on a medium coincident to the diffraction grating;
    measuring by at least one of a linear array detector and a two-dimensional array detector, spatial distribution of intensity of the electromagnetic wave that is diffracted into at least the $1^{st}$ and higher diffraction orders or the $-1^{st}$ and lower diffraction orders; and
    further determining by the at least one linear array detector and two-dimensional array detector, the wavelength spectrum of the electromagnetic wave that is coupled to the surface plasmon by measuring the spatial distribution of intensity of the diffracted electromagnetic wave.

2. The method according to claim 1, wherein the electromagnetic wave is simultaneously made incident on a plurality of such diffraction gratings or on different areas of one of the diffraction gratings.

3. The method according to claim 1, further comprising:
    emitting the electromagnetic wave from electromagnetic radiation sources comprising a plurality of monochromatic sources or at least one polychromatic source.

4. The method according to claim 1, wherein the diffraction grating comprises at least one of a metal diffraction grating and a diffraction grating coated with a metal layer.

5. The method according to claim 4, wherein the coated metal layer comprises one or more layers.

6. The method according to claim 1, further comprising:
    at least a portion of the diffraction grating is coated with a layer of selected substances.

7. The method according to claim 1, wherein the at least one of a linear array detector and a two-dimensional array detector further comprises at least one of a CCD, PDA, and CMOS detector module.

8. The method according to claim 1, wherein the diffraction grating comprises a sensing element on a surface plasmon resonance sensor to detect chemical and biological substances.

9. A system for spectroanalyzing surface plasmons, comprising:

an electromagnetic radiation module to make a collimated electromagnetic wave incident on a diffraction grating, wherein excitation of surface plasmons on a medium coincident to the diffraction grating and dispersion of a wavelength spectrum of the electromagnetic wave through diffraction by the diffraction grating are simultaneously caused; and at least one of a linear array detector and a two-dimensional array detector to measure spatial distribution of intensity of the electromagnetic wave that is diffracted into at least the $1^{st}$ and higher diffraction orders or the $-1^{st}$ and lower diffraction orders and that is projected onto different areas of the position-sensitive detector, and to further determine the wavelength spectrum of the electromagnetic wave that is coupled to the surface plasmon by measuring the spatial distribution of intensity of the diffracted electromagnetic wave.

10. The system according to claim 9, wherein the electromagnetic wave is simultaneously made incident on a plurality of such diffraction gratings or on different areas of one of the diffraction gratings.

11. The system according to claim 9, wherein the electromagnetic radiation module comprises:
a plurality of monochromatic sources; or
at least one polychromatic source to emit the electromagnetic wave.

12. The system according to claim 9, wherein the at least one of a linear array detector and a two-dimensional array detector further comprises at least one of a CCD, PDA, and CMOS detector module.

13. The system according to claim 9, wherein the diffraction grating comprises at least one of a metal diffraction grating and a diffraction grating coated with a metal layer.

14. The system according to claim 13, wherein the coated metal layer comprises one or more layers.

15. The system according to claim 9, further comprising:
at least an area on a surface of the diffraction grating is coated with a layer of selected substances.

16. The system according to claim 9, wherein the diffraction grating comprises a sensing element on a surface plasmon resonance sensor to detect chemical and biological substances.

17. A method for constructing a surface plasmon resonance sensor, comprising:
forming a sensor element with diffraction gratings arranged to simultaneously excite surface plasmons and disperse electromagnetic waves over a wavelength spectrum through diffraction on the diffraction gratings;
providing an adjustment to the diffraction gratings to control spatial distribution of wavelength intensity of the dispersed electromagnetic waves; and
orienting the at least one of a linear array detector and a two-dimensional array detector to measure the spatial distribution of intensity of the electromagnetic wave that is diffracted into at least the $1^{st}$ and higher diffraction orders or the $-1^{st}$ and lower diffraction orders and that is projected onto different areas of the position sensitive detector, and to further determine by the at least one of a linear array detector and a two-dimensional array detector, the wavelength spectrum of the electromagnetic wave that is coupled to the surface plasmon by measuring the spatial distribution of intensity of the diffracted electromagnetic wave, wherein the position sensitive detector comprises one of a linear array detector and a two-dimensional array detector.

18. The method according to claim 17, wherein the at least one of a linear array detector and a two-dimensional array detector further comprises at least one of a CCD, PDA, and CMOS detector module.

19. The method according to claim 17, wherein the diffraction gratings comprise at least one of metal diffraction gratings and diffraction gratings coated with a metal layer.

20. The method according to claim 19, wherein the coated metal layer comprises one or more layers.

21. The method according to claim 17, further comprising:
providing at least an area on the sensor element that is coated with a layer of selected substances.

22. The method according to claim 17, further comprising:
adjusting the diffraction gratings based on at least one of geometry, orientation, and quantity.

23. A system for constructing a surface plasmon resonance measurement sensor, comprising:
a sensor element with diffraction gratings arranged to simultaneously excite surface plasmons and disperse electromagnetic waves over a wavelength spectrum through diffraction on the diffraction gratings, wherein the diffraction gratings are adjustable to control spatial distribution of wavelength intensity of the dispersed electromagnetic waves; and
the at least one of a linear array detector and a two-dimensional array detector oriented to measure the spatial distribution of intensity of the electromagnetic wave that is diffracted into at least the $1^{st}$ and higher diffraction orders or the $-1^{st}$ and lower diffraction orders and that is projected onto different areas of the at least one of a linear array detector and a two-dimensional array detector, and to further determine the wavelength spectrum of the electromagnetic wave that is coupled to the surface plasmon by measuring the spatial distribution of intensity of the diffracted electromagnetic wave.

24. The system according to claim 23, wherein the at least one of a linear array detector and a two-dimensional array detector further comprises at least one of a CCD, PDA, and CMOS detector module.

25. The system according to claim 23, wherein the diffraction gratings comprise at least one of metal diffraction gratings and diffraction gratings coated with a metal layer.

26. The system according to claim 25, wherein the coated metal layer comprises one or more layers.

27. The system according to claim 23, an area on the sensor element is coated with a layer of selected substances.

28. The method according to claim 23, further comprising:
adjusting the diffraction gratings based on at least one of geometry, orientation, and quantity.

* * * * *